United States Patent
Shomrony et al.

(10) Patent No.: US 7,924,420 B2
(45) Date of Patent: Apr. 12, 2011

(54) OPTICAL INSPECTION INCLUDING PARTIAL SCANNING OF WAFERS

(75) Inventors: Gilad Shomrony, Kfar-Saba (IL); Arnon Gratch, Tel Aviv (IL); Shai Silberstein, Rishon-Le-Zion (IL)

(73) Assignee: Applied Materials South East Asia Pte. Ltd., Singapore (SG)

( * ) Notice: Subject to any disclaimer, the term of this patent is extended or adjusted under 35 U.S.C. 154(b) by 252 days.

(21) Appl. No.: 11/764,296

(22) Filed: Jun. 18, 2007

(65) Prior Publication Data
US 2008/0307908 A1 Dec. 18, 2008

(51) Int. Cl.
*G01N 21/88* (2006.01)

(52) U.S. Cl. .................... 356/237.5; 382/144

(58) Field of Classification Search .... 356/237.2–237.6; 382/144–151
See application file for complete search history.

(56) References Cited

U.S. PATENT DOCUMENTS

| 2005/0195389 | A1* | 9/2005 | Noy et al. | 356/237.2 |
| 2006/0279729 | A1* | 12/2006 | Heiden et al. | 356/237.5 |
| 2007/0038325 | A1* | 2/2007 | Guldi et al. | 700/110 |

OTHER PUBLICATIONS

U.S. Appl. No. 10/345,097, filed Jan. 15, 2003, Furman et al.

* cited by examiner

*Primary Examiner* — Gregory J Toatley
*Assistant Examiner* — Rebecca C Slomski
(74) *Attorney, Agent, or Firm* — SNR Denton US LLP

(57) ABSTRACT

Inspection of objects, such as semiconductor wafers, can be performed using a diluted scan wherein not all of an inspected area is actually imaged. Instead, a dilution plan can be devised based on the desired amount of area to be skipped and the particular parameters of the inspection, such as the size of each unit area to be imaged or not imaged and the distribution features of the wafer. When the same area is inspected in multiple wafers, the wafers can be inspected in sets using a dilution plan whereby a wafer (or inspected area) can be statistically inspected using diluted scans of the set of wafers. Similarly a die or group of dies of a specified type can be statistically inspected using diluted scans of a set of dies (or group of dies). When statistical inspection is used, the end results of such inspections, such as defect densities and distributions, can be corrected to account for inaccuracies that may be introduced when certain portions are imaged more often than others due to the dilution plan.

21 Claims, 15 Drawing Sheets

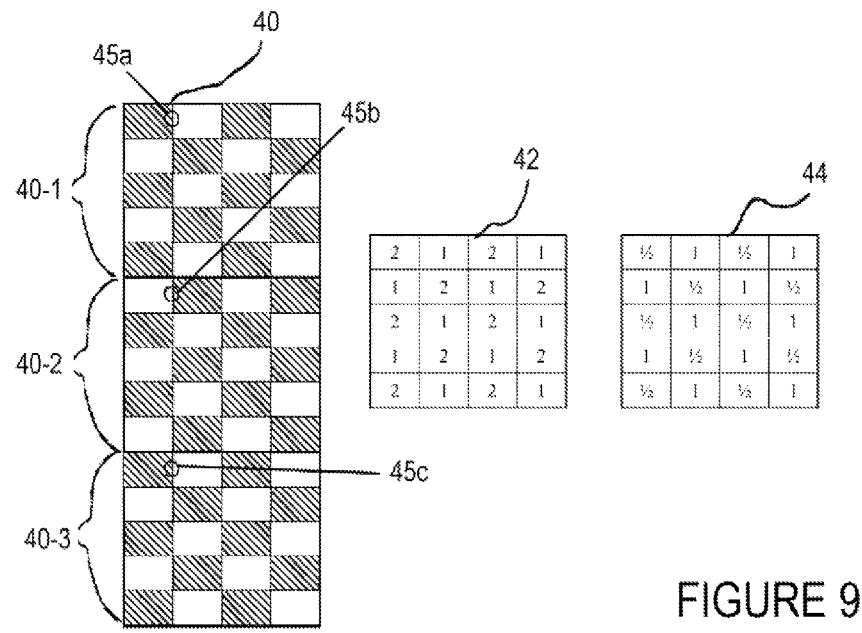
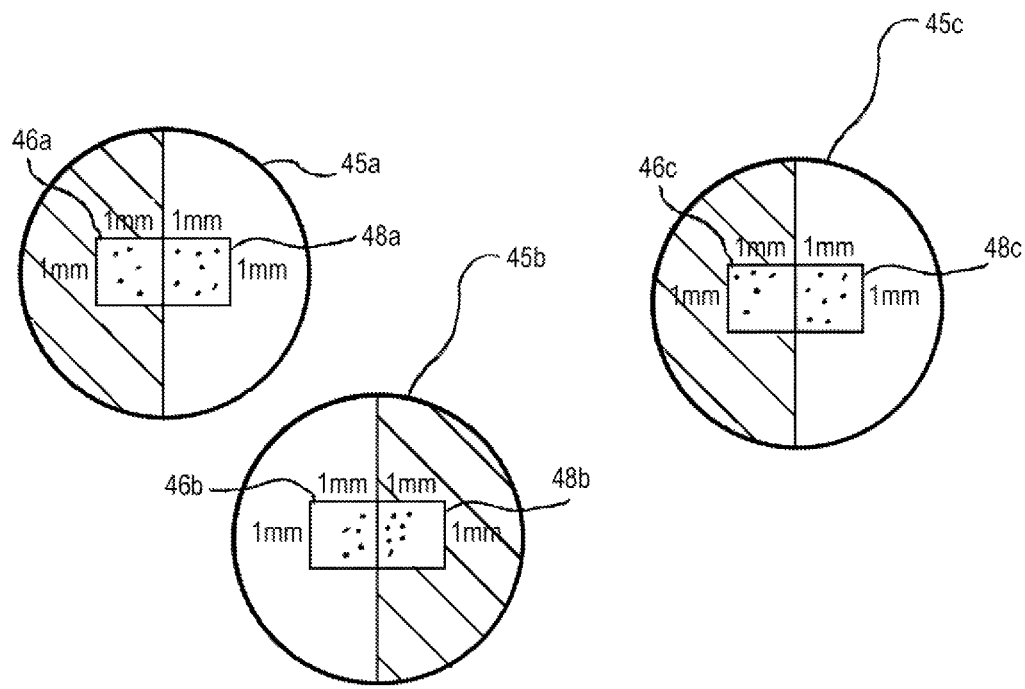
FIGURE 9

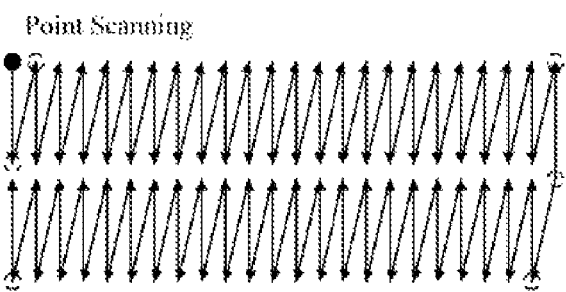
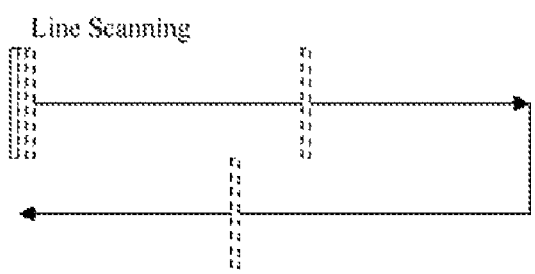
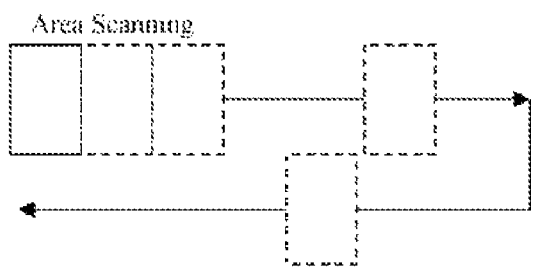
FIGURE 11

OPTICAL INSPECTION INCLUDING PARTIAL SCANNING OF WAFERS

FIELD OF THE INVENTION

The present invention relates generally to inspection of objects, for example, semiconductor wafers, using optical inspection tools.

BACKGROUND

Inspection of semiconductor wafers (and other objects, such as reticles, flat-panel displays, photomasks, and the like) often involves scanning the entire wafer or other object. Generally speaking, there are three main types of scanning, which are shown in FIG. 11. For instance, in point scanning, the instantaneous field of view comprises a single point and the scanning is carried out by applying a saw-like relative movement between the wafer and the illumination/detection point. In line scanning, the instantaneous field of view comprises a narrow line of pixels. Wafer scanning is carried out by applying a raster-like relative movement between the wafer and the detector. In area scanning, the instantaneous field of view comprises a two-dimensional area and the scanning is carried out by applying a discrete raster-like relative movement between the wafer and the detector.

Optical wafer inspection can require a relatively long period of time, especially when high magnification is used. Presently, throughput of only a few wafers per hour is common. Where throughput needs to be increased, the inspection operator faces a limited number of choices. For example, lower magnification can be used so that a larger area is included in the instantaneous field of view. However, due to the lower magnification, smaller defects may be missed.

Another option is to scan only a part of the wafer. Examples of partial scanning include scanning some, but not all of a wafer based on a (manual and/or automatic) designation. For instance, FIGS. 12A-12B show scanning of some dies, but not other dies. FIG. 12A shows an inspection in which alternating rows of dies 12 in a wafer 10 are scanned. Other partial scans are possible. FIG. 12B shows an inspection in which the top half, but not the bottom half, of a wafer 10 is scanned. FIG. 12C shows an inspection in which part of every die is scanned, namely an inspection where every other slice of a wafer 10 is scanned.

However, the use of partial scanning runs the risk that an area comprising a defect may be missed entirely if the area is included in a part of the wafer that is not scanned.

SUMMARY

Some embodiments of the present subject matter include methods and systems whereby inspection throughput can be increased via the use of improved partial scanning techniques. For instance, in some embodiments, partial scanning can increase throughput by scanning fewer slices, which decreases scanning time (and thus can raise throughput) by reducing slice transitions. In some embodiments, partial scanning can increase throughput by scanning fewer frames or areas within a slice, which can decrease scanning time (and thus raise throughput) by allowing for the use of a higher scanning velocity. In other embodiments, slice and frame dilution can be combined. However, in contrast to existing types of dilution, in some embodiments of the present subject matter, the advantages of dilution can be obtained without great sacrifices in inspection accuracy or quality.

Generally, the subject matter can be implemented using any suitable optical inspection tool. However, the subject matter may be especially advantageous in 2-D imaging applications. Since, in many cases, statistics regarding defect data are more relevant than detection of each and every defect, partial scans that will produce statistical data representative of the entire wafer (or inspected portions of the entire wafer) can be used. In embodiments of the present subject matter, the scanning is diluted parallel to the slice direction and, in some embodiments, parallel and perpendicular to the slice direction.

BRIEF DESCRIPTION OF THE SEVERAL VIEWS OF THE DRAWINGS

A full and enabling disclosure including the best mode of practicing the appended claims and directed to one of ordinary skill in the art is set forth more particularly in the remainder of the specification. The specification makes reference to the appended figures, in which:

FIG. 9 shows an exemplary set of diluted frames and related defect density correction data;

FIG. 11 comprises three examples of scanning techniques; and

Use of like reference numerals in different features is intended to illustrate like or analogous components.

DETAILED DESCRIPTION OF THE PREFERRED EMBODIMENTS

Figure 1:
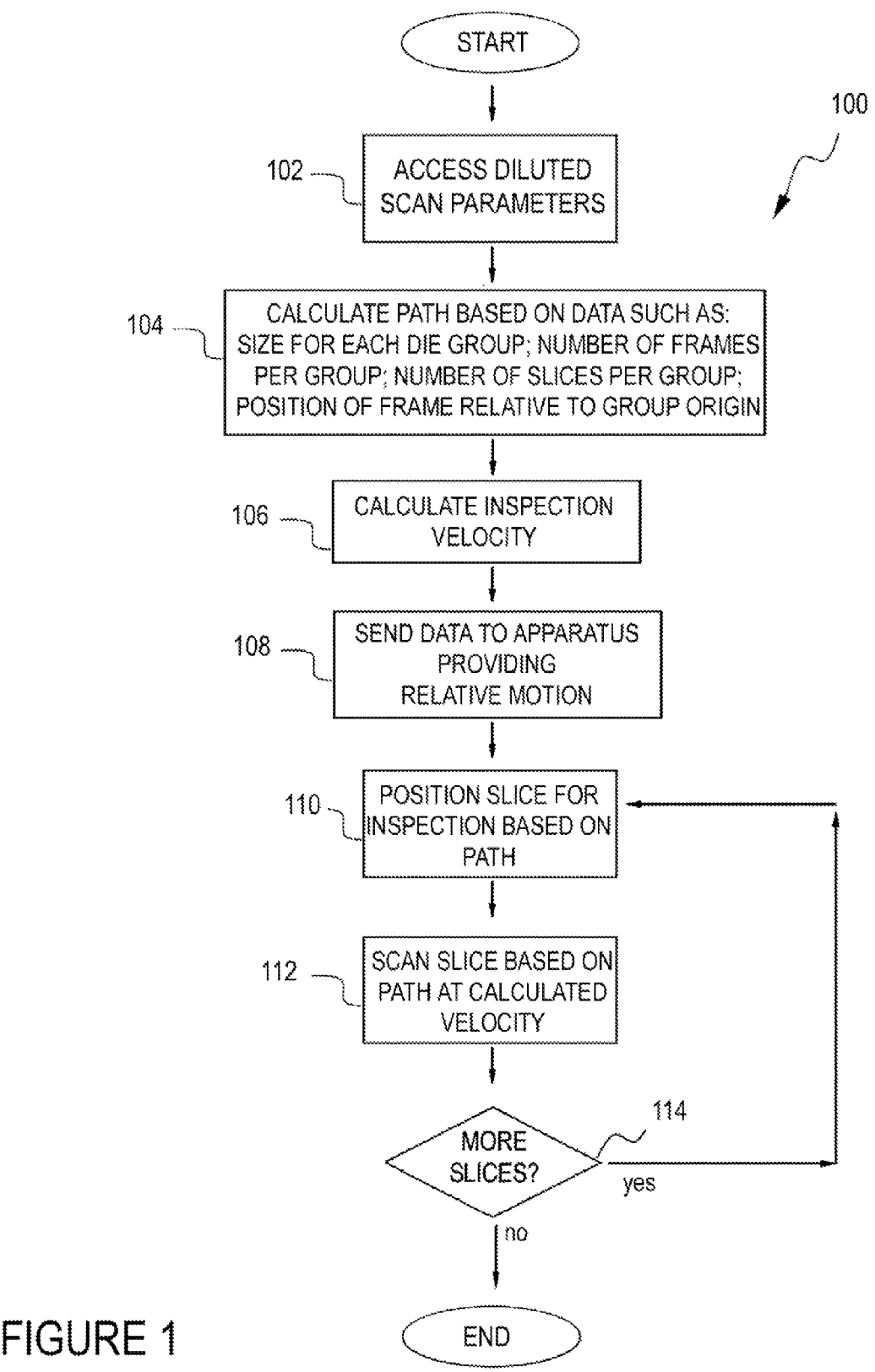
FIG. 1 is a flowchart illustrating steps in an exemplary process for performing a diluted scan as part of an optical inspection.

Reference will now be made in detail to various and alternative exemplary embodiments and to the accompanying drawings, with like numerals representing substantially identical structural elements. Each example is provided by way of explanation, and not as a limitation. In fact, it will be apparent to those skilled in the art that modifications and variations can be made without departing from the scope or spirit of the disclosure and claims. For instance, features illustrated or described as part of one embodiment may be used on another embodiment to yield a still further embodiment. Thus, it is intended that the present disclosure includes modifications and variations as come within the scope of the appended claims and their equivalents.

A method of optical inspection can comprise positioning at least one wafer for inspection by an optical inspection tool and performing a diluted scan of at least one slice of the wafer lying along a scanning axis so at least ten percent of the total area of the at least one slice is not imaged. Placement and scanning will depend on the tool. For instance, in some tools, the wafer may be moved by a stage along an inspection path. In other tools, the wafer may remain stationary while the wafer is scanned along an inspection path by adjusting optical components (such as mirrors) to vary the field of view of the tool. In any event, performing a diluted scan can comprise scanning a plurality of areas in at least one slice and imaging some, but not all, of the areas in the slice. As will be discussed below, in some embodiments, the areas may comprise frames or inspection tool fields-of-view.

In some embodiments, the inspection can include performing a diluted scan of multiple slices. The scan may be performed so that the dilution effects occur perpendicularly to the scanning axis as well as parallel to the scanning axis. Perpendicular dilution may be an express part of the diluted scan in some embodiments. For instance, the scanning of multiple slices may be performed so that at least one imaged area in one of the slices is at a different location along the scanning axis than at least one area imaged in the second slice. In some embodiments, one or more slices may be scanned so that essentially twenty-five percent, fifty percent, or seventy-five percent of the area of the wafer designated for inspection is imaged. The area designated for inspection may comprise a part or parts of the wafer or may comprise the entire wafer.

A method of optical inspection can comprise accessing data comprising an inspection recipe, the recipe designating at least a portion of a wafer of a defined type for inspection. The portion may comprise the entire wafer or one or more parts thereof. The method may further comprise performing a diluted scan of the designated portion of each of a plurality of wafers of the defined type. The scan can comprise scanning a plurality of areas in at least one slice of each wafer and imaging some, but not all, areas in the slice. Furthermore, the diluted scan may be performed so that, as between at least two wafers, at least one area imaged in the first wafer is not imaged in the second wafer. In some embodiments, all of the areas imaged in at least a first wafer may differ from those imaged in the second wafer. However, the scans can be performed so that the imaged areas from the diluted scans of the plurality of wafers, if taken in combination, represent essentially the entire portion designated for inspection. In some embodiments, not only will all of the areas comprising the portion designated for inspection be imaged once, but some areas may be imaged multiple times.

A method for optical inspection can comprise accessing data comprising an inspection recipe designating at least a portion of a wafer for inspection. The designated portion can comprise an entire wafer or less than an entire wafer, and the portion can comprise a plurality of ideally-identical regions. For example, the regions may comprise identical wafer dies. The method can further include performing a diluted scan of the designated portion of the wafer, including scanning a plurality of areas in at least one slice and imaging some, but not all of the areas. The imaged areas may be evaluated for the presence of defects. Any suitable technique or techniques may be used. For each defect that lies within a region, the method can further comprise determining where the defect lies relative to a region reference point. For instance, the reference point may comprise an origin for the region, such as the corner of a die (if the region comprises a die). Then, each defect from a plurality of regions can be projected into a single projected region based on each defect's determined location relative to the region reference point. The method can further comprise correcting data regarding the projected defects based at least in part on the number of times the portion of the region containing each defect is included in an imaged area.

For instance, the method can comprise calculating at least one defect density for at least one part of the region based on determining a total number of projected defects in the at least one part of the region and the number of times the part of the region containing the defect was scanned. For instance, each part may comprise a square millimeter in a die. In some embodiments, the method can comprise calculating a plurality of defect densities for a plurality of square millimeter parts of a die.

A method of inspecting a plurality of wafers can comprise accessing data comprising an inspection recipe designating at least a portion of a wafer of a defined type for inspection. The portion may comprise the entire wafer or less than the entire wafer. The method can further include performing a diluted scan of the designated portion in each of a plurality of wafers of the defined type, including scanning a plurality of areas in at least one slice of each wafer and imaging some, but not all, of the areas in the slice(s). Based on the imaged areas, the method can further include evaluating the portion designated for inspection for the presence of defects. Then, the location of each defect relative to a wafer reference point, such as an origin point, can be determined. The method can further include projecting each defect into a single projected wafer based on each defect's determined location. The method can further comprise correcting data regarding the projected defects based at least in part on the number of times each portion of the wafer is included in an imaged area. For instance, if a wafer defect density is calculated, then calculating can include weighing the defect count in each portion of the wafer by a factor derived from the number of times the portion of the wafer containing the defect was imaged relative to the number of other portions in the wafer.

Embodiments of the methods and variants thereof can be implemented using any suitable inspection tool. For instance, an inspection apparatus can comprise an imager and at least one illumination source. The inspection apparatus can be configured to performed a diluted scan of at least one slice of a wafer along a scanning axis so that at least ten percent of the total area of the at least one slice is not imaged by scanning a plurality of areas in at least one slice and imaging some, but not all, of the areas. Additionally, the subject matter can be applied in inspection of not only wafers, but of other objects such as reticles, flat-panel displays, photomasks and the like. Therefore, it is intended that the term "wafer" be viewed broadly.

In the following examples, several terms will be used for ease of explanation. In the examples below, a "frame" is use to refer to a unit imaging area for the inspection tool. In a diluted scan, some, but not all, frames (or other suitable areas) may not be imaged, while some are. A "slice" is a group of adjacent frames along a scanning axis. In some embodiments, the "inspection path" is the path over which the inspection occurs from beginning to end. For instance, the inspection path may comprise several slices, with each slice comprising a plurality of frames. For example, the inspection path may follow a first slice of a wafer from left to right, a second slice from right to left, a third slice from left to right, and so on in a serpentine fashion so that a plurality of parallel slices are scanned. However, other path shapes could be used other than serpentine.

Generally speaking, in some embodiments, an inspection tool performs an inspection by scanning different areas of the wafer. For instance, the field of view of the tool may be changed relative to wafer location by moving the wafer. Additionally or alternatively, depending on the tool, other components (such as lenses or mirrors in the imager or elsewhere) may be adjusted to change the field of view. The areas that are to be imaged (and the areas not to be imaged) can be specified so as to define an inspection path. For instance, the tool may access a list of frames (or other areas) that are to be inspected, with the list of frames (or other areas) determined based on desired dilution parameters.

FIG. 1 is a flowchart illustrating steps in an exemplary process flow 100 for performing a diluted scan. At step 102, diluted scan parameters are accessed from memory or another suitable source. For instance, a wafer inspection recipe may define a dilution plan or desired dilution parameters for an inspection run. For example, the parameters may comprise data that indicates the amount of dilution and/or desired distribution for imaged and non-imaged frames and/or slices. Based on the dilution parameters, at step 104, the inspection tool calculates an inspection path. In some embodiments, the inspection may be based on evaluating dies or groups of dies for defects. The inspection path can be based on parameters comprising: the desired size for each die (or other area) group, the number of frames or other imaging unit areas per group, the number of slices per group, and the position of each frame (or other imaging area) relative to the group origin. Then, at step 106, the inspection velocity is calculated. For instance, if the inspection tool uses a stage to support and position the wafer, the stage velocity can be determined. As another example, if the tool uses mirrors, lenses, and/or other optics to vary the view of the wafer, then the velocity for such component(s) may be determined.

Once the inspection path and inspection velocity are calculated, at step 108 data is sent to the stage and/or other components used to vary the area viewed by the imager. In some embodiments, the inspection path data can comprise a list of slices. For each slice, the data can comprise the starting position, end position, and a list of the frames along the slice. Based on the inspection path and velocity data, the stage (and/or other components) can position the wafer so that the frames (or other areas) designated for inspection are brought into view. Alternatively, other components in the tool may be positioned to bring areas of the wafer into view. When inspected frames (or other areas) are in view, illumination, imaging, and/or other signals may be sent in order to image the frames (or other areas) designated for inspection.

For instance, at step 110, initially, the first slice of the wafer is brought into position and at step 112, a plurality of areas of the slice, such as frames, are scanned along a scanning axis, with some frames being imaged and some frames not being imaged according to the inspection path data. For instance, the stage and/or imager components can be configured so that the field of view of the imager moves from one area, such as a frame, to the next within a slice. In an inspection tool that uses pulsed illumination, a suitable pulse can be provided with appropriate timing along with signals to imaging components such as detectors in order to ensure that each area that is to be imaged is illuminated. The pulse may or may not be provided when a non-imaged frame is in the field of view. Of course, other illumination systems may be used. The imaged frames can be stored in memory, such as an input buffer and/or at other suitable location(s) for use in the remainder of the inspection process. After scanning of the slice is complete, then at 114 the tool determines if more slices remain to be scanned (for example, determining whether further slices are identified in a list of inspected frames). If one or more slices remain, the wafer (and/or tool optics) is positioned to scan the next slice of the wafer at 110 and 112. If no more slices remain, then the inspection is complete for that wafer.

Exemplary processes and orders of operation such as discussed above are for purposes of example only. In other embodiments, the order of steps may be changed, steps may be combined, steps may be split into sub-steps, and/or some steps may be performed in parallel.

Figures 2A, 2B:
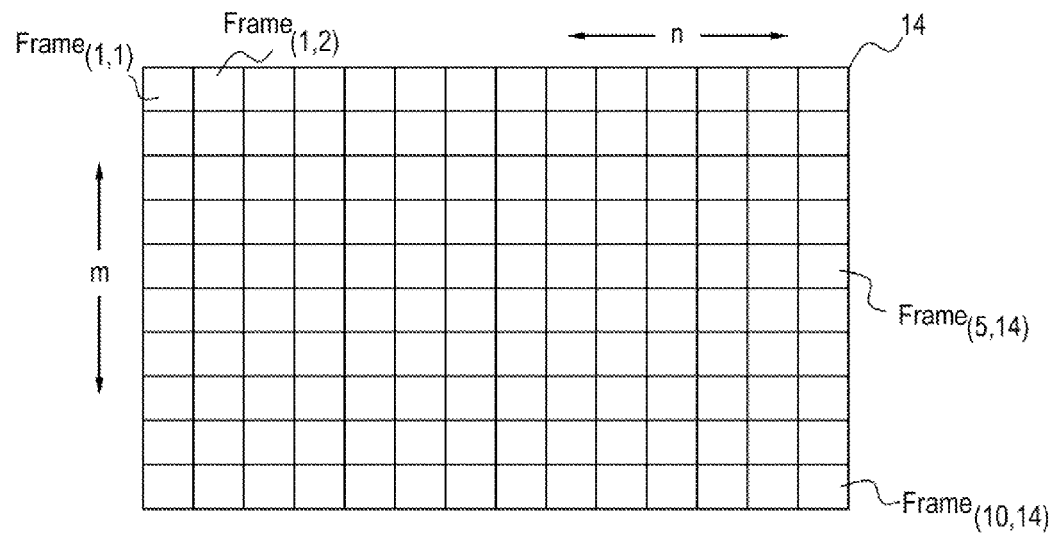
FIGS. 2A, 2B, and 2C represent exemplary arrangements of dies and a frame overlay.

FIG. 2 is a group of diagrams showing an exemplary set of areas that may be the subject of a diluted scan. In this example, each area comprises a frame. In FIG. 2A, twenty-four dies (labeled 12a through 12x) are shown. FIG. 2A further indicates that the dies are grouped into four groups (Group I, II, III, and IV). For instance, some inspection tools may compare a grouping of dies to another grouping of dies to determine potential defects. Other tools may compare dies one at a time, in larger or smaller groups, or based on groupings other than dies, of course. FIG. 2B illustrates an overlay of frames (generally denoted as 14). In this example, frame overlay 14 comprises an array of frames arranged into m rows and n columns, with m=10 and n=14. For purposes of the present discussion, reference to a particular frame will take the form Frame(m,n).

Figure 2C:
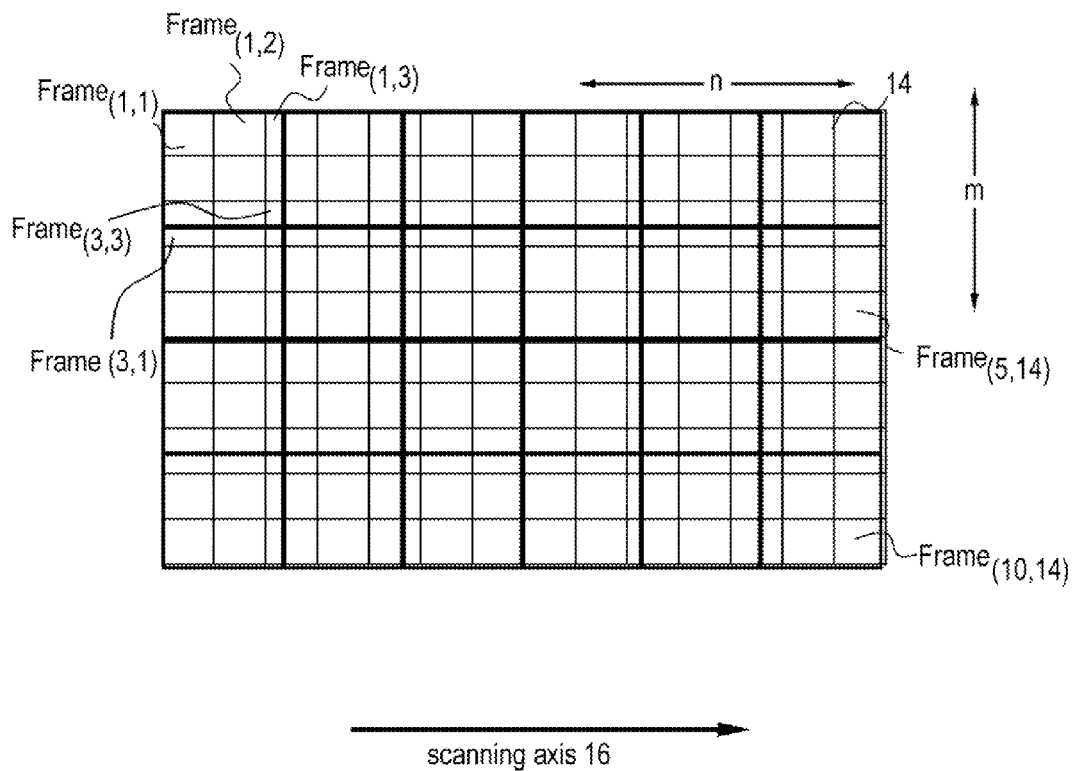

FIG. 2C illustrates the overlay of frames 14 onto the dies of FIG. 2A. Although the die labels are not shown in FIG. 2C, the dies are separated by thick lines, with thin lines indicating the frames. Where only a thick line is seen, the frame and die boundaries overlap. As can be seen in FIG. 2C, some frames (such as Frame(1,1) and Frame(1,2)) lie entirely within a single die; some frames(such as Frame(1,3)) span two dies adjacent to one another along the scanning axis; further frames (such as Frame(3,1)) span two dies adjacent to one another in a direction perpendicular to the scanning axis; and still further frames (such as Frame(3,3)) span multiple dies. In this example, a scanning axis is indicated at 16 and is parallel to the rows m. Thus, each row m represents a slice of the portion of the wafer that is to be imaged.

As an example, a diluted scan starting at row 4 may begin at Frame (4,1), proceed to Frame (4,3), Frame (4,5), and so on until Frame (4,13) is reached. Then, if the next slice is row 5 (i.e. there is no slice dilution or the slice dilution calls for rows 4 and 5 to be scanned), the scan may begin at Frame (5,14), then move to Frame(5,12), to Frame (5,10), and so on to Frame(5,2) if the inspection path is serpentine.

In several of the examples herein, the frames are square-shaped. However, the particular frame size and shape may vary according to the construction and configuration of the particular inspection tool. The number of frames imaged at one time may vary. Some tools may be capable of imaging a single frame or multiple frames at once. Additionally, in this example, the grid of dies is parallel to the grid of frames. However, the dies or other features may be at a different angle relative to the grid of frames. Thus, it is not intended for the present subject matter to be limited by the shape, arrangement, or size of the frames (or other areas) comprising slices or the layout of the particular wafer (or other object) that is inspected.

Generally speaking, the inspection tool can be configured so that dilution can be specified as a percentage of the area of the wafer (or the percentage of the inspected area of the wafer) that is not to be imaged. For instance, the amount of area that is not imaged can be 10%, 25%, 50%, 75%, or any other fraction of the inspected area. The dilution is carried out by "removing" areas, such as frames, from the inspection by not imaging those areas (frames). Of course, while performing a diluted scan, depending on the tool configuration and operation, the non-imaged frames may be briefly in view of the imaging apparatus as the tool moves from an imaged frame to the next imaged frame.

Figure 3A:
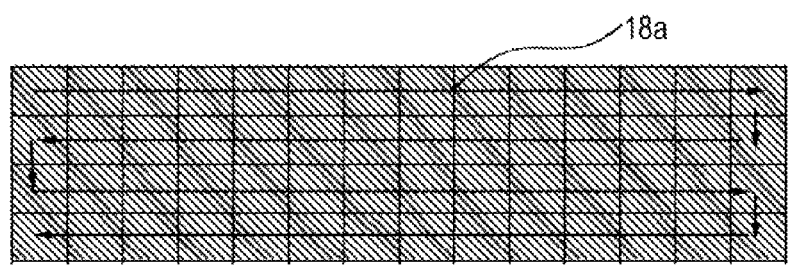
FIGS. 3A, 3B, 3C, and 3D represent examples of no dilution, slice only dilution, frame-only dilution, and slice/frame dilution, respectively.

FIGS. 3A, 3B, 3C, and 3D are diagrams illustrating general dilution principles. In these examples, a grid of frames where m=4 and n=14 is shown covering twelve dies, with scanned frames are shaded. FIG. 3A is provided to illustrate the case where no dilution occurs. Thus, inspection path 18*a* is shown as a serpentine path beginning at Frame(1,1) and continuing until Frame(4,1) with all scanned frames imaged.

Figure 3B:
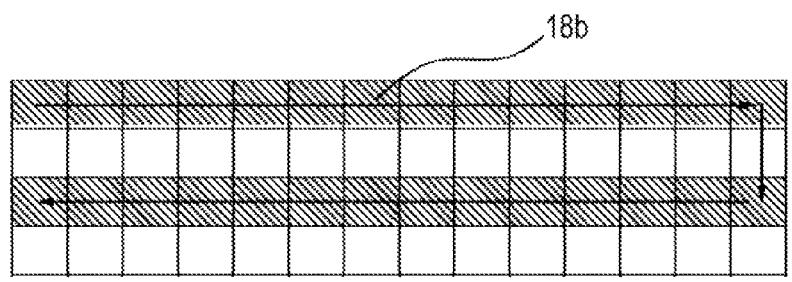

FIG. 3B illustrates slice dilution wherein entire slices are skipped. In this example, the slices comprising frames in rows 2 and 4 are skipped entirely; the frames in rows 2 and 4 are not imaged and, in this example, are not scanned, either. Instead, once Frame (1,14) is reached, inspection path 18*b* skips to Frame (3,14), which is the next imaged frame in this dilution plan. In this example, the scan is diluted in a direction perpendicular to scanning axis 16. For instance, Frame(1,14) is imaged, but perpendicularly-adjacent Frame(2,14) is not, and so on.

Figure 3C:
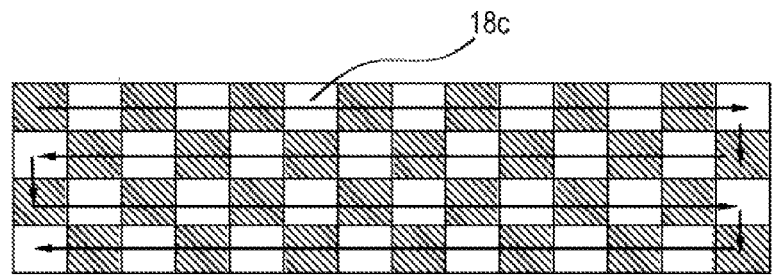

FIG. 3C illustrates an example of what is termed "frames dilution." Inspection path 18*c* is shown as passing through every slice, but not every frame in each slice along the inspection path is imaged. Instead, in this example, every other frame is imaged. The scan begins at Frame(1,1), which is imaged. Then, the next frame is Frame(1,2), which is not imaged, followed by Frame(1,3), which is imaged, and so on. In this example, the scan itself is diluted in a direction parallel to the scanning axis. Although in this example the imaged frames are also adjacent to non-imaged areas in a direction perpendicular to the scanning axis, this is not to be confused with slice dilution. For example, in some frame dilution schemes, it is possible for one or more imaged frames in a slice to be perpendicularly-adjacent to imaged frames in another slice.

Figure 3D:
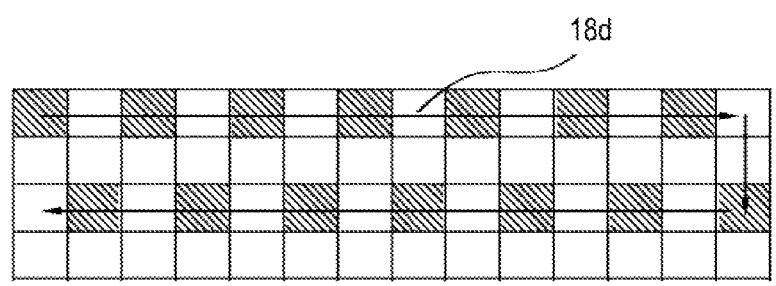

FIG. 3D illustrates a dilution plan comprising both frame dilution and slice dilution. In inspection path 18*d*, the serpentine path begins at Frame (1,1) and proceeds next to frame (1,3), and so on until frame(1,13). Then, the path moves to Frame (3,14), thus skipping all frames (2,n). Thus, the scan is diluted both in a direction parallel to the scanning axis and perpendicular to the scanning axis.

As noted above, the particular selection of frames for imaging is set forth by a dilution plan. Since a diluted inspection by definition will not image all of the wafer, then it is likely that some defects will not be imaged. In a bad dilution plan, certain types of defects or clusters of defect may not be detected since such defects/clusters are not imaged. However, defects may be inferred from statistical analysis of imaged defects, provided, though, that the imaged area is spread homogenously on the wafer (or inspected part of the wafer). Therefore, a goal met by some embodiments of the present subject matter is to have a homogenous dilution so that the detected defects provide a valid statistical base for evaluating the total extent of defects on the wafer.

Several examples of poor dilution plans may be illustrative. For example, if 50% dilution is used, several possible dilution plans risk missing significant defects. For example, if only one die out of two is inspected, then a defective die may be missed and/or large clusters of defects within a non-imaged die (or non-imaged dies) may be missed. If only one slice out of two is inspected, then a horizontal scratch (i.e. a scratch parallel to the slice direction) in a non-scanned slice may be missed. If fifty percent of all the dies are inspected (such as the dies in the top half of a wafer), then all defects located in the non-inspected half (the bottom half in this example) may be missed.

Therefore, some embodiments of the present subject matter utilize dilution plans/algorithms that are based on one or more of the following principles, which are not presented in any particular order. As noted earlier, in many cases statistics regarding defects, such as defect density within a die, can be of interest in an inspection. However, in order for the statistics to be useful, the underlying data must be reliable. Thus, the following principles can be used to guide practice of the present subject matter in order to achieve better inspection results. Several principles, of course, may be applicable regardless of whether statistical analysis of defects is used. Additionally, the principles are not meant to be limiting, and the present subject matter is intended to include embodiments without regard to the extent the principles discussed below are satisfied.

First, full die coverage is desirable. That is, it is desirable to inspect all parts of a "representative" die at least once in the course of an inspection. Second, it is desirable for uniform die coverage; that is, it is desired for each part of a die to be inspected by essentially the same number of frames (or other area units). Third, it is desirable for the distance between frames in a given slice to be equal, since non-equal distances can complicate imager triggering, illumination control, and/or aspects of the inspection. Fourth, it is desirable for the distance between frames in different slices to be equal, since non-equal distance can also complicate illumination as well as the control of the stage and/or other apparatus used to change the frame in view of the imager. Finally, in some embodiments, it is preferable for the number of frames in a group of dies to be an even number, such as for 50% frame dilution. Furthermore, in some embodiments, such as for 25% and 75% frames dilution, it is preferable for the number of frames evenly divisible by 4. Divisibility by two (and/or four) can allow for comparison between frames from successive groups when such comparisons are used in evaluating a potential defect, such as when groups of dies are compared to other groups of (inspected or reference) dies.

An additional consideration in dilution planning is system resources and time for inspection. Generally, for inspection that uses slices, the time for an inspection comprises the time taken to scan the slices and the time taken in transitioning between slices. The scanning time per slice depends on factors including the scanning velocity and the length of the slice, while the transition time between slices depends generally on the number of slices. If slices are diluted, the time required to scan each slice remains, but the transition time is reduced. As an example, in 50% dilution, the number of slices may be halved, which can result in half the number of transitions. If frames only are diluted, then the inspection stage (and/or other apparatus used to change the inspection view) can be moved faster, thus reducing the time to scan each slice. However, the full number of slice transitions will remain. For instance, in 50% frame dilution, the time to scan each slice is halved when compared to no dilution, but the transition time remains the same, so the total time is slightly larger than 50% of the time for a non-diluted scan.

Thus, for instance, slice dilution is generally fastest, since the inspection requires fewer slice transitions. Slice/frame dilution is slower than slice dilution only, and frame dilution only is the slowest. On the other hand, scanning more slices results in a better spread of inspected (imaged) frames. Additionally, in some frame dilution modes, the number of imaged frames in any given slice can be reduced significantly and the scanning speed may be increased. However, limitations can arise. For instance, some frame dilution modes and magnification combinations may require a scanning speed that reaches or exceeds the maximum speed of the tool. For example, if the tool uses a stage to impart relative motion between the wafer and imager, the stage may have a maximum speed that limits the potential dilution modes.

In some embodiments, the choice of a dilution methodology can further be based on the magnification of the inspection tool. For example, in the Negevtech 3100 inspection tool, several magnification modes are available. For instance, super magnification may be provided using an HS100 lens, high magnification with an M200 lens, medium magnification with a M340 lens, and low magnification with an HT550 lens. In some embodiments of the present subject matter, the desired coverage amount and magnification may result in the following matrix of dilution methodologies:

| "Magnification"/ Dilution | 25% | 50% | 75% |
|---|---|---|---|
| "Super" | Frame Dilution Only | Frame Dilution Only | Slice Dilution Only |
| "High" | Frame Dilution Only | Frame Dilution Only | Slice Dilution Only |
| "Medium" | Slice & Frame Dilution | Frame Dilution Only | Slice Dilution Only |
| "Low" | Slice Dilution Only | Slice Dilution Only | Slice Dilution Only |

However, magnification may be controlled using other lenses, combinations of lenses, or other suitable means in any suitable tool. Additionally, the table above is not meant to be limiting, and in other embodiments, any suitable dilution methodology may be used for any desired area of coverage at any magnification level Additional considerations may be involved in devising a desirable dilution plan. For instance, in some embodiments, better spread is achieved by using a dilution plan where every non-imaged frame is adjacent to at least one other imaged frame, with horizontal or vertical adjacency preferable to diagonal adjacency. Better spread may be achieved if imaged frames are not adjacent to other imaged frames. In some embodiments, it may be advantageous for the frame and slice positions used in a diluted scan to correspond to the same physical locations relative to the wafer as the frame and slice positions in a non-diluted scan. This may achieve repeatability in results and/or facilitate easier comparison of results between diluted and non-diluted inspections. In some embodiments of inspection tools, defect detection may be carried out by comparing groups of dies to other groups of dies and/or reference groups of dies. Thus, for such inspection tools, embodiments of the dilution algorithm may be directed to obtaining full and uniform group of die coverage and not just die coverage. In some embodiments, dilution plan for one type of dilution may be derived based on the dilution plan for another dilution. For example, rather than determining an imaged frame layout for seventy-five percent dilution, the imaged frame layout for twenty-five percent dilution may be completely inverted.

Several examples of slice, frame, and slice and frame dilution will be discussed below. These examples show only a brief portion of the wafer showing a distribution of scanned and non-scanned slices. However, the slices may extend farther along the scanning axis and the particular lengths shown are for purposes of example only. Furthermore, although these examples discuss slice-only dilution, it will be apparent that the principles of slice dilution may be combined with other dilution, such as frame dilution. Frame and slice dilution will be discussed further below. In the following examples, slice numbers are identified using the variable n, which represents an integer.

Figure 4:
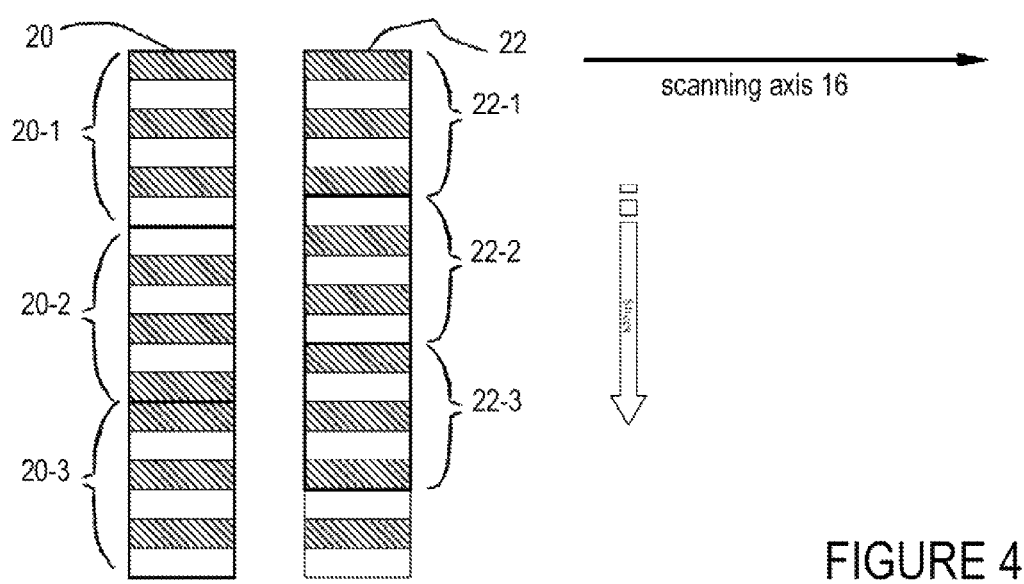
FIG. 4 shows exemplary results of an algorithm for slice dilution.

Turning to FIG. 4, two die groups sets, 20 and 22, are shown. The groups of dies within each set are separated by thick lines. Each die group set 20 and 22 is shown with certain slices shaded and other slices unshaded to illustrate 1:2 (fifty percent) dilution using slice dilution only. Scanning axis 16 is illustrated along with an arrow labeled "slices" to indicate the slice direction (i.e. parallel to the scanning axis).

In this example, die group set 20 comprises three die groups 20-1, 20-2, and 20-3, while die group set 22 comprises three die groups 22-1, 22-2, and 22-3. Each die group may comprise one or more dies. In die group set 20, each group of dies 20-1, 20-2, and 20-3 comprises six slices. In die group set 22, each group of dies 22-1, 22-2, and 22-3 comprises five slices. Generally speaking, when a group of dies (such as the die groups in set 22) comprise an odd number of slices (2n+1), then every other slice should be scanned through the entire set of die groups. This is shown in die group set 22 with the alternating shading of die groups 22-1, 22-2, 22-3, and the partial group shown below 22-3. For the die groups in set 22, n=2.

When inspecting a set of wafers that each include an odd number of slices in each group, the first scanned slice of the first group can alternate between wafers, while scanned slices alternate within each wafer as noted above. For instance, in a first wafer, the first scanned slice can comprise slice 1, while in a second wafer, the first scanned slice can comprise slice 2.

For groups of dies having an even number of slices (2n), every other slice in each group is scanned, and the arrangement of scanned slices alternates between groups. For a first group, the scanned slices begin at slice 1 and continue to slice 2n−1. For a second group, the scanned slices begin at slice 2n+2 and continue to 2n+4, 2n+6, etc. until 4n is reached. For instance, in group 20-1, the scanned slices are 1, 3, and 5. Then, in group 20-2, the scanned slices are 8, 10, and 12.

Similar principles can be used when multiple wafers of the same type are inspected. For instance, in a first wafer, the first group of slices can begin at slice 1 and alternate, with the scanned slices alternating between groups in the first wafer. Then, for a second wafer, the first group of scanned slices begins at slice 2 and continues to 4, 6, etc. until 2n is reached, and the second group of slices begins at slice 2n+1 and continues to 2n+3, 2n+5, etc until 4n−1 is reached.

Figure 5:
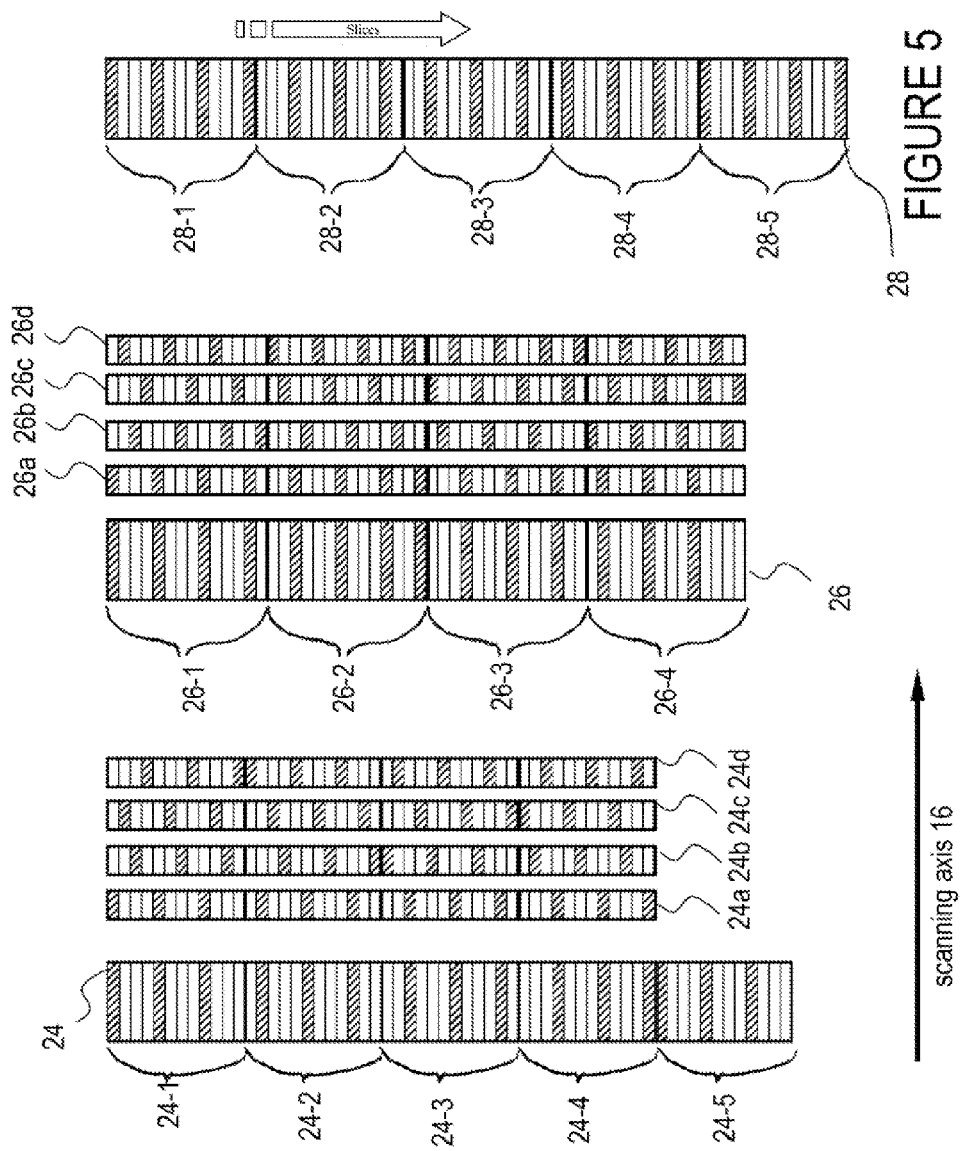
FIG. 5 shows additional exemplary results of an algorithm for slice dilution.

FIG. 5 shows several examples of slice dilution in a 1:4 (25%) dilution scheme whereby twenty-five percent of the inspected area is imaged. Die group set 24 shows a plurality of die groups 24-1, 24-2, 24-3, 24-4, and 24-5 each comprising twelve slices. Die group set 26 shows a plurality of die groups 26-1, 26-2, 26-3, 26-4 each comprising fourteen slices. Die group set 28 shows a plurality of die groups 28-1, 28-2, 28-3, 28-4, and 28-5 each comprising thirteen slices.

Dilution for a die group having an odd number of slices, such as those shown in set 28, will first be addressed. Generally, if a group of dies has an odd number (4n+1 or 4n+3, for example) of slices, then every fourth slice is scanned. Furthermore, when scanning multiple wafers, the slice arrangements are adjusted so that the first slice in each set of four wafers is different. For instance, if slice 1 is the first slice scanned in the first wafer, then slice 2 will be the first slice scanned in the second wafer, slice 3 is first scanned in the third wafer, and slice 4 is the first slice scanned in the fourth wafer. For a fifth wafer, the first scanned slice returns to 1, and so on.

However, in some embodiments, it may be advantageous to configure the tool for better distribution when only two wafers in a set or 4p+2 wafers in a set, where p is another integer. For instance, the inspection may start with slice 1 for the first wafer, but with the scanning of the second wafer starting with slice 3. Then, scanning of the third wafer can start from slice 2, with scanning of the fourth wafer starting from slice 4.

If the group of dies comprises an even number of slices, then twenty-five percent diluted scanning takes a more complex form. Generally, a complete iteration of the scanning set comprises a set of four die groups. For a group of dies having $4n$ slices, the scanned slices are:

1, 5, 9, . . . $4n-3$; $4n+2$, $4n+6$ . . . $8n-2$; $8n+3$, $8n+7$ . . . $12n-1$; $12n+4$, $12n+8$, . . . $16n$

An example of this is shown in FIG. 4 at die group 24, where each die group comprises twelve slices ($4n$, where $n=3$) and the die groups 24-1, 24-2, 24-3, and 24-4 comprise a full iteration of slice arrangements. Die group 24-5 is shown to illustrate that the slice arrangement iteration begins again. FIG. 5 additionally shows four more die group sets 24*a*, 24*b*, 24*c*, and 24*d*, which each represent the slices scanned in an exemplary first, second, third, and fourth wafer in a set of four wafers. The scanned slices are as follows for each wafer (I through IV) in the set:

4 are imaged. Thus, for any given pair of groups adjacent in the slice direction, the imaged frames are also opposite. For instance, the imaged frames in groups 30-2 and 30-3 are the inverse of one another. For cases in which a group of dies comprises an even number of slices, the distribution is more complex. For instance, for a group of dies comprising an even number of slices, if the rule were for adjacent slices to have opposite imaged frames, then each group of dies would have the same imaged frames. Instead, for groups of dies having an even number of slices such as those groups in set 32, the imaged frames are selected so that the imaged frames alternate between slices within a group and frames imaged in any two groups adjacent in the slice direction (i.e. perpendicular to the scanning axis 16) are opposite.

Furthermore, whether the number of slices in a group is odd or even, in some embodiments, the imaged frames are alternated for every other wafer when sets of wafers of the same type are inspected. For example, in a set of wafers, the first row of the first wafer may be scanned as shown in the first row of group 30-1 (if an odd number of slices is to be used) or as shown in the first row of group 30-2 (if an even number of slices is to be used). In the second wafer of the set, the first row

| I: | 1, 5, 9 . . . , $4n-3$; | $4n+2$, $4n+6$ . . . , $8n-2$; | $8n+3$, $8n+7$ . . . , $12n-1$; | $12n+4$, $12n+8$ . . . , $16n$ |
|---|---|---|---|---|
| II: | 3, 7, 11 . . . , $4n-1$; | $4n+4$, $4n+8$ . . . , $8n$; | $8n+1$, $8n+5$ . . . , $12n-3$; | $12n+2$, $12n+6$ . . . , $16n-2$ |
| III: | 2, 6, 10 . . . , $4n-2$; | $4n+3$, $4n+7$ . . . , $8n-1$; | $8n+4$, $8n+8$ . . . , $12n$; | $12n+1$, $12n+5$ . . . , $16n-3$ |
| IV: | 4, 8, 12 . . . , $4n$; | $4n+1$, $4n+5$ . . . , $8n-3$; | $8n+2$, $8n+6$ . . . , $12n-2$; | $12n+3$, $12n+7$ . . . , $16n-1$ |

However, a group of dies with an even number of slices may be of the form $4n+2$. For a group of dies having $4n+2$ slices, the scanned slices are also distributed across a set of four die groups, and the scanned slices are:

1, 5, 9, . . . $4n+1$; $4n+5$, $4n+9$ . . . $8n+1$, $8n+4$; $8n+8$, $8n+12$ . . . $12n+4$; $12n+8$, $12n+12$ . . . $16n+4$

An example of this is shown in FIG. 4 at die group 26, where each die group comprises fourteen slices ($4n+2$, where $n=3$) and the die groups 26-1, 26-2, 26-3, and 26-4 comprise a full iteration of slice arrangements. FIG. 4 additionally shows four more die group sets 24*a*, 24*b*, 24*c*, and 24*d*, which each represent the slices scanned in an exemplary first, second, third, and fourth wafer in a set of four wafers. The scanned slices are as follows for each wafer (I through IV) in the set:

would be scanned as shown in the second row of group 30-1 (if an odd number of slices are to be used) or in the second row of group 30-2 (if an even number of slices is to be used).

Figure 7:
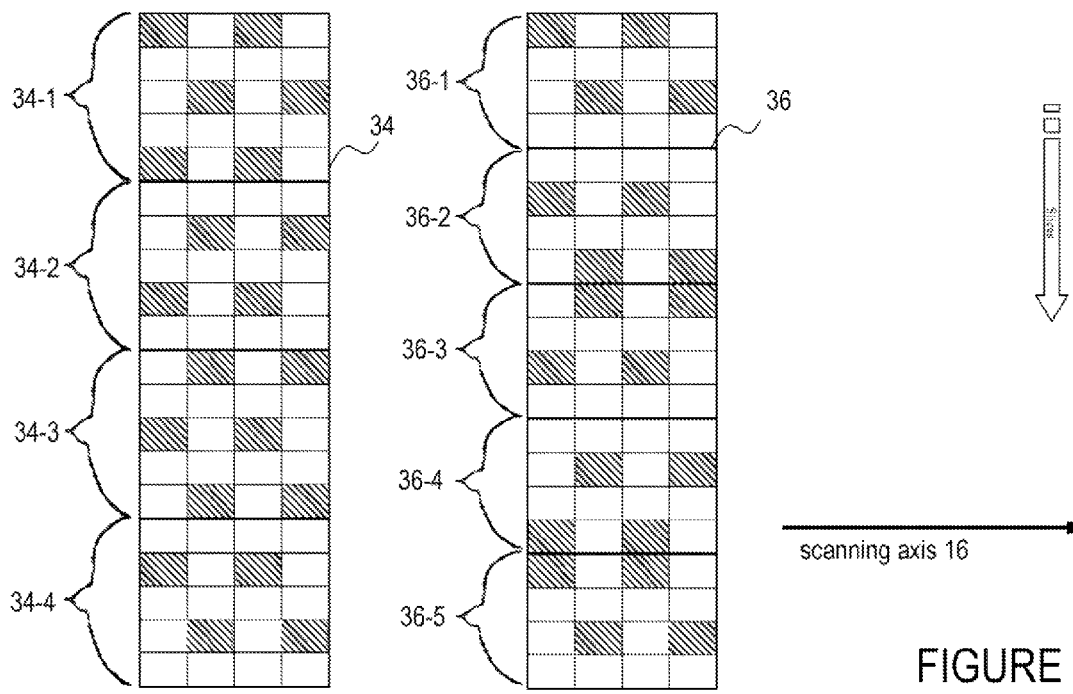
FIG. 7 shows exemplary results of an algorithm for frame and slice dilution.

FIG. 7 shows an embodiment whereby twenty five percent (1:4) dilution is achieved through a combination of (1:2) frame dilution and (1:2) slice dilution. The slices are scanned in the manner outlined above for (1:2) slice dilution, while in each slice only half of the frames are imaged in a manner outlined above for (1:2) frame dilution. For instance, as shown in die group set 34, each die group 34-1, 34-2, 34-3, and 34-4 has five slices. Every other slice comprises imaged frames, with the imaged frames alternating between each slice. Put another way, the frame dilution along a serpentine

| I: | 1, 5, 9 . . . , $4n+1$; | $4n+5$, $4n+9$ . . . , $8n+1$, $8n+4$; | $8n+8$ . . . , $12n+4$; | $12n+8$, $12n+12$ . . . , $16n+4$ |
|---|---|---|---|---|
| II: | 3, 7, 11 . . . , $4n-1$, $4n+2$; | $4n+6$, $4n+10$ . . . , $8n+2$; | $8n+6$, $8n+10$ . . . , $12n+2$; | $12n+7$, $12n+11$ . . . , $16n+7$ |
| III: | 4, 8 . . . , $4n$; | $4n+4$, $4n+8$ . . . , $8n$; | $8n+5$, $8n+9$ . . . , $12n+5$; | $12n+9$, $12n+13$ . . . , $16n+5$, $16n+8$ |
| IV: | 2, 6, 10 . . . , $4n-2$; | $4n+3$, $4n+7$ . . . , $8n+3$; | $8n+7$, $8n+11$ . . . , $12n+3$, $12n+6$; | $12n+10$, $12n+14$ . . . , $16n+6$ |

Figure 6:
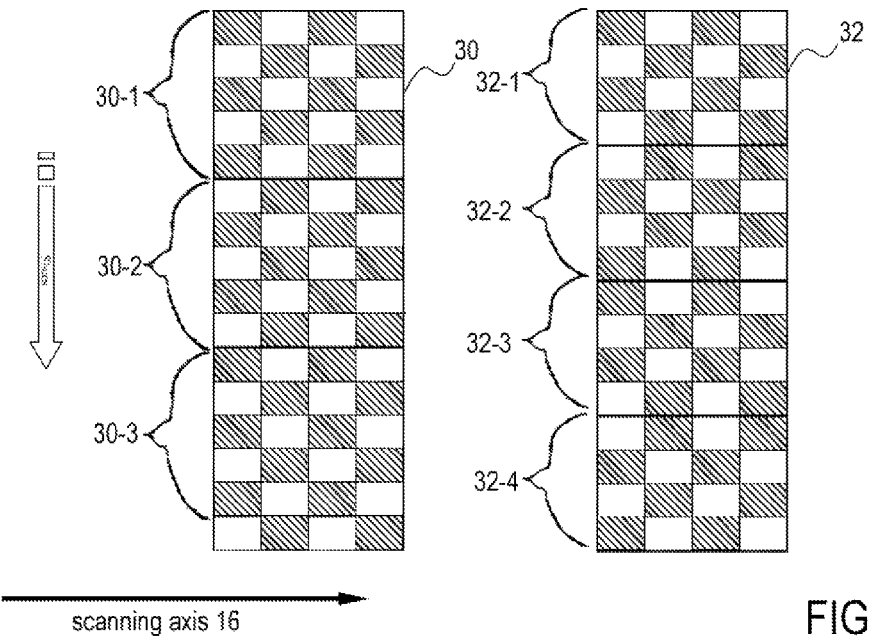
FIG. 6 shows exemplary results of an algorithm for frame dilution.

Turning now to FIGS. 6 and 7, examples of frame and slice dilution will be discussed. FIG. 6 shows two die group sets 30 and 32 in order to illustrate which frames are to be imaged in fifty percent (1:2) dilution using frame dilution. The imaged frames are shaded. Die group set 30 comprises die groups 30-1, 30-2, and 30-3. Each die group in set 30 comprises an odd number of slices, in this example, five slices. Die group set 32 comprises die groups 32-1, 32-2, 32-3, and 32-4. Each die group in set 32 comprises an even number of slices, in this example, four slices.

For cases in which a group of dies comprises an odd number of slices, for any given pair of adjacent slices, the opposite frames are imaged. For instance, in slice 1 of group 30, frames 1 and 3 are imaged, while in slice 2 of group 30, frames 2 and path in each group is apparent, with the serpentine path skipping (in this example) every other slice.

For die groups such as 36-1, 36-2, 36-3, and 36-4, the dilution plan is more complex. If a group of dies has an even number of slices, two principles apply. The first principle is that the scanned slices are selected so that for each pair of groups adjacent in the slice direction, the opposite slices are scanned in each group. For instance, the first and third slices in group 36-1 are scanned, while the second and fourth slices of group 36-2 are scanned. Similarly, the first and third slices of group 36-3 are scanned, while the second and fourth slices of group 36-4 are scanned. The second principle is that, as between two adjacent pairs of groups, the opposite frames in the scanned slices of those groups are imaged. For instance, the first slice in group 36-1 features imaged frames that are the opposite of the first slice of group 36-3. The imaged frames of the fourth slice of group 36-2 are the opposite of the imaged frames of the fourth slice in group 36-4.

When scanning sets of wafers, an exemplary dilution plan can provide for the first wafer to be scanned such as is shown in FIG. 7; the second wafer to be scanned by imaging the same frames but in inverse slices to FIG. 7; the third wafer to be scanned using inverse frames and inverse slices to those shown in FIG. 7; and the fourth wafer to be scanned using inverse frames but the same slices as shown in FIG. 7.

Figure 8:
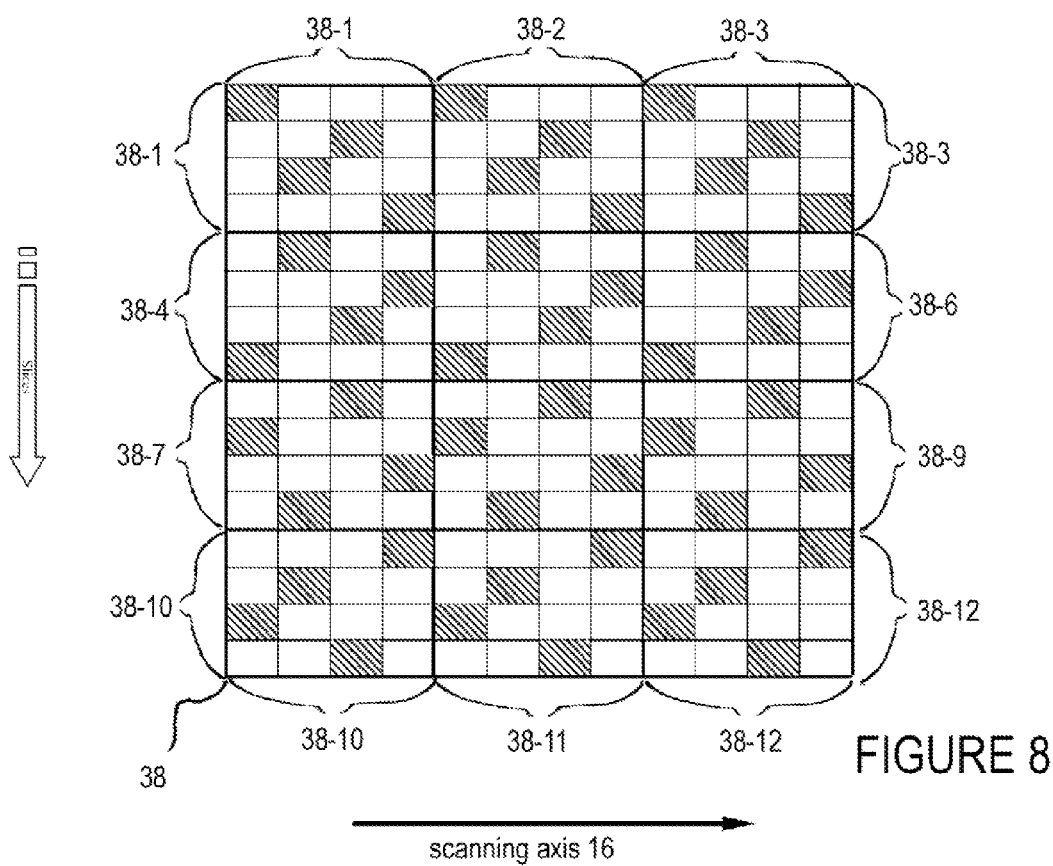
FIG. 8 shows exemplary results of an algorithm for frame-only dilution.

FIG. 8 shows another embodiment whereby twenty five percent (1:4) dilution is achieved, this time by using (1:4) frame dilution only. FIG. 8 shows a set of die groups 38, namely die groups 38-1, 38-2, 38-3, 38-4, 38-5, 38-6, 38-7, 38-8, 38-9, 38-10, 38-11, and 38-12. Although not labeled in FIG. 8, group 38-5 lies between 38-4 and 38-6 and group 38-8 similarly lies between group 38-7 and 38-9. Also, FIG. 8 illustrates how, as noted above, the arrangement of frames within a group can be repeated for groups that are adjacent along the scanning axis.

Starting with the imaged frames shown in groups 38-1, 38-2, and 38-3, the position of the imaged frame in each respective slice is offset by one frame in the scanning axis direction for every 4 slices (4n slices if the group of dies contains 4n slices). For instance, Frame(1,1) is the first frame imaged in slice 1. In slice 5, the first imaged frame is Frame(5,2). In slice 9, the first imaged frame is Frame(9,3), and in slice 13, the first imaged frame is Frame(13,4), and so on. If an imaged frame lies at the edge of a group, then in the fourth (4nth) slice afterwards, the first imaged frame is the first frame in the fourth (4nth) slice after. For example, Frame (1,4) is the first imaged frame in slice 4. For n=4, in slice 20, the first imaged frame is Frame (20,1). In embodiments using 1:4 frame dilution and a stage moving the wafer, the stage may be operated at about four times the normal operating rate, which may advantageously increase throughput.

When multiple wafers of the same type are inspected, the first group of dies in the first wafer can be inspected using a frame formation based on the formation shown in group 38-1. In the first group of dies in the second wafer, the frame formation used can be based on the formation shown in group 38-4. In the third wafer, the frame formation for the first group of dies is based on the formation shown in group 38-7. In the fourth wafer, the frame formation for the first group of dies is based on the formation shown in group 38-10.

In some embodiments, an inspection tool may report results based on a defect density. For instance, rather than (or in addition to) reporting the locations of defects across a wafer, die, group of dies, region, etc., the inspection tool may alternatively or additionally determine the number or density of defects in an area or region. This can be achieved, for instance, by dividing a region into parts and then counting the number of defects within each part. For example, in some embodiments, it is preferable to report defect density within a die in terms of the number of defects per square millimeter (mm) in a die by counting the number of defects in each square millimeter. In some cases, it may be advantageous to report defect density for a particular type of die rather than (or in addition to) reporting defect density for every instance of a die.

However, if dilution is used, then problems can arise. For example, not all areas of all instances of a given die type will be inspected the same number of times. For example, due to the dilution, some areas may be imaged more than others. If the densities for all parts are considered equally, then the inspection results may be inaccurate. Therefore, in some embodiments of the present subject matter, defect density values can be corrected based on the number of times a particular area is in an imaged frame.

FIG. 9 is an illustration of a set of die groups 40 comprising die groups 40-1, 40-2, and 40-3. For ease of explanation, assume for the following examples that each of die groups 40-1, 40-2, and 40-3 may comprise a single die. Matrix 42 illustrates a count of the number of times a respective frame images a portion of the die. For instance, in this example, dies 40-1 and 40-3 are imaged using the same imaged frame formation, while die 40-2 is imaged using the inverse imaged frame formation. Thus, in this example, areas of the die of type 40 corresponding to Frame(1,1), Frame(1,3), and so on are imaged twice as much as areas in the die corresponding to Frame(1,2), Frame(1,4), etc. This is shown at 42, which represents a count of the number of each times a frame has been imaged. At 44, FIG. 9 shows a series of density correction values that can be used to correct data related to detected defects in a set of frames. Although in this example, frames are imaged one or two times, the actual number of times different frames are imaged can vary. Additionally, while only two different counts are shown in this example, more variety in the number of times frames are imaged may occur (for example, a first frame could be imaged once, a second frame three times, a third frame six times, etc.). Generally, the correction factor for each frame corresponds to 1/(number of times the frame was imaged). Of course, it is to be understood that the particular frame counts, defect distributions, and defects of this example are hypothetical and for purposes of explanation.

For example, a particular piece of each die is shown in an enlarged view, with 45a corresponding to an enlarged view of the border between Frame (1,1) and Frame (1,2) of die 40-1, 45b corresponding to an enlarged view of the border between Frame (1,1) and Frame (1,2) of die 40-2, and 45c corresponding an enlarged view of the border between Frame (1,1) and Frame (1,2) of die 40-3.

In each enlarged view, two particular parts are shown, part 46, which lies in the area covered by Frame (1,1) and part 48, which lies in the area covered by Frame (1,2). Parts 46a and 48a are in die 40-1, parts 46b and 48b are in die 40-2, and parts 46c and 48c are in die 40-3.

In this example, each of parts 46 and 48 is a square millimeter. Furthermore, the number of defects in part 46 is equal to five and the number of defects in part 48 is equal to seven. In this example, the defects are shown as dots, but the defects may take any number of forms or shapes. Also, although parts 46 and 48 are shown at the border between frames, this is for purposes of example only. Although only single parts are shown, a distribution of densities in several parts for the area in a frame may be calculated. For example, for Frame (1,1), a distribution of densities comprising a density for each square mm within Frame (1,1) may be calculated. The same principles for correcting a single density are applicable to correction of multiple densities, but a single density is used for ease of explanation.

A truly "representative" result should indicate a defect density of 5 defects/mm$^2$ in part 46 and a density of 7 defects/mm$^2$ in part 48. In some embodiments, this defect density can be determined by counting the number of defects in each part and projecting the count into a corresponding part in a representative die. The projection can be based by determining the relative location of each part to a respective origin point within each die. For instance, each part 46a, 48a, 46b, 48b, and 46c, 48c may be defined based on coordinates within the die, such as based on distance from the die corner.

In this example, the five defects from part 46a and the five defects from part 46c can be projected into a corresponding part 46 in a representative die with a total defect count of 10. The seven defects from part 48b can be projected into a corresponding part 48 in the representative die, which will have a total defect count of 7 for part 48. Then, the total counts for each part can be corrected based on the number of times the area in which each part lies was imaged.

For instance, the area in which part 46 lies was imaged twice, namely in dies 40-1 and 40-3. The area in which part 48 lies was imaged once, in die 40-2. The density correction values shown in matrix 44 can be applied to correct the counts to obtain proper values. In this example, the correction value for Frame (1,1) is equal to one half (½). Thus, the total count for each part in the area covered by Frame (1,1) can be halved. The total count of ten for part 46 is thus corrected to five, and therefore a correct density of 5 defects/mm$^2$ for part 46 is obtained. The total count of seven for part 48 is not changed (the correction factor is one), so the correct density of 7defects/ mm$^2$ for part 48 is obtained.

The same principles can be applied when defect density is calculated based on inspections across multiple wafers. For example, each of dies 40-1, 40-2, and 40-3 may be imaged from the same wafer and/or from different wafers. Although presented in the context of correcting defect densities within a die, the densities may be determined based on other regions. For example, defect distribution across a wafer of a certain type can be determined by projecting defects counted in inspections of a plurality of different wafers into a single wafer by determining the relative location of each defect in its respective wafer. Then, the defect density can be weighed based on the number of times the area of the wafer comprising the defects was included in an imaged frame.

Figure 10A:
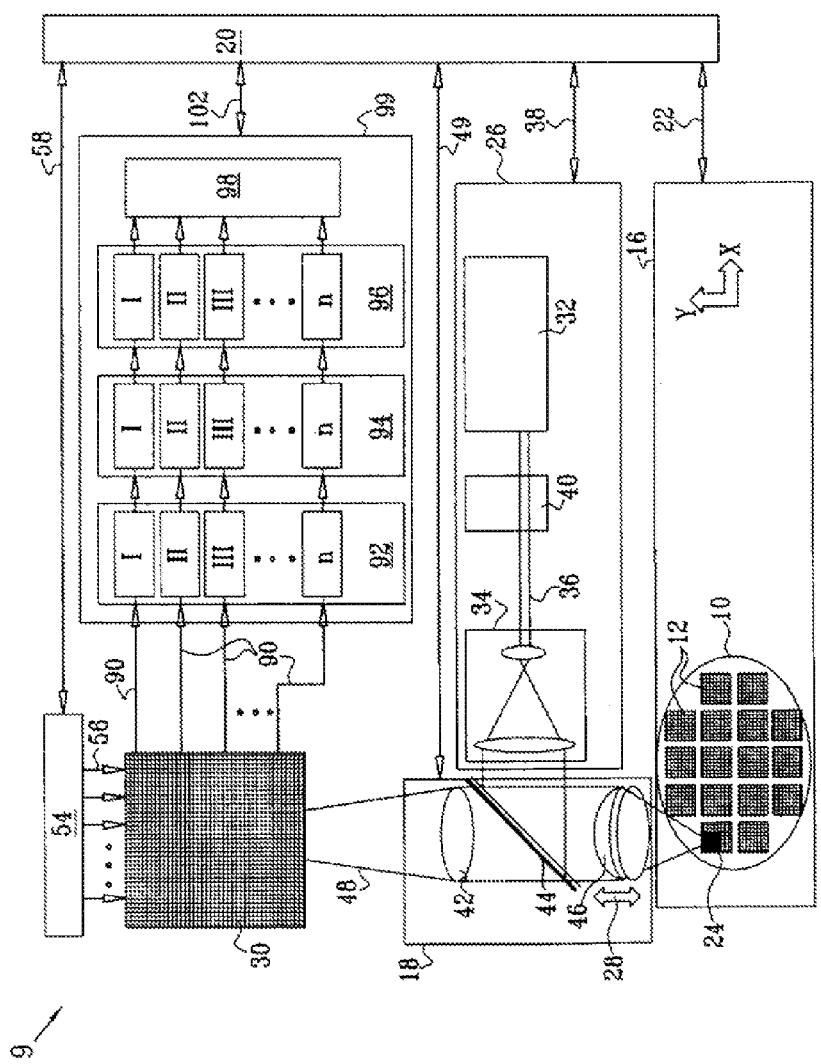
FIG. 10A is a block diagram of components in an exemplary optical inspection system.

FIG. 10A is a block diagram showing components in an exemplary optical inspection tool. The present subject matter may be implemented by configuring any suitable inspection tool, and the tool briefly discussed below is for purposes of illustration only. For instance, the tool may comprise a Negevtech 3100 optical inspection tool (available from Negevtech, Ltd. of Rehovot, Israel) configured to support diluted scanning in accordance with one or more of the embodiments discussed herein. Discussion of exemplary embodiments of an inspection tool can be found in Negevtech U.S. Pat. No. 7,525,659, filed Jan. 23, 2003, which is incorporated by reference herein in its entirety. Of course, regardless of the type of tool, the tool can be configured for desired operation using suitable hardware and/or software.

As shown in FIG. 10A, a patterned semiconductor wafer 10 featuring a plurality of wafer dies 12, is placed and aligned on a continuous moving XY translation stage 16 to impart motion between the wafer and the components used to image the wafer. XY translation stage 16 moves wafer 10 typically in a serpentine pattern beneath an optical imaging system 18. However, other movement patterns could be used. Additionally, the wafer may be moved in a different manner in other embodiments. Furthermore, in some embodiments, the wafer may remain stationary, with relative motion between the wafer and component(s) used to image the wafer being imparted by the use of one or more optical components. For instance, a rotating mirror can be used to move the field of view of imaging system 18 in a serpentine pattern across the wafer. In other embodiments, relative motion may be imparted by moving both the wafer and adjusting optical components.

Movement of XY translation stage 16 (and therefore movement of wafer 10) is synchronized with action of a multi-component camera system by a central control system 20 via control/data links 22, in such a way that wafer 10 moves the equivalent of one field of view 24 during a CCD matrix photo-detector frame time. For example, the frame time and motion may be synchronized so that the wafer moves only on the order of about 10$^{-2}$ of a single pixel during exposure to an illumination system 26, thereby resulting in little to no image smear or loss of image resolution.

An illumination system 26 is provided, and can include a repetitively pulsed laser 32, a laser beam expander 34, a laser beam light path 36, and control/data links 38 as shown in FIG. 10A. Regardless of the type of illumination, pulsed illumination enables ultra fast imaging of a large field of view 24, by featuring pulsed laser 32 for repetitively generating and propagating a highly bright and highly energetic light pulse in an extremely short period of time. Illumination system 26 is in communication with the central control system 20 via control/data links 38.

In system 9, pulse rate, i.e., pulses per second, of pulsed laser 32 is synchronized with frame speed of the array of individual matrix photo-detectors of focal plane assembly 30. A laser pulse, illuminating field of view 24 of a wafer die 12 for a time duration of microseconds to nanoseconds (compared to milliseconds frame time of temporally gated camera system focal plane assembly 30 of matrix photo-detectors), results in instantaneous illumination of field of view 24 of an inspected wafer die 12. In one very short laser pulse, a relatively large number of pixels, for example, about forty eight million pixels, of focal plane assembly array 30 can be simultaneously illuminated, and there is essentially no relative movement among the pixels. The laser light pulse duration is preferably shorter than the image pixel dwell time or about the same order of magnitude to the pixel dwell time, where the pixel dwell time refers to the time a point on the wafer is imaged by a detector pixel while the wafer is moving. The pulse and imaging rate can depend on the speed at which the tool is operating. For instance, as noted above, in some embodiments, an inspection velocity is calculated for implementing a dilution plan. The pulse and imaging rate can be timed to image frames in the list of imaged frames based on the calculated velocity.

An optical imaging system can include a focusing lens 42, a beam splitter 44, an objective lens 46, and control/data links 49. This system is suitable for ultra fast high resolution synchronous imaging of high magnification, for example, 50× of wide field of view 24 of one or more wafer die(s) 12. An automatic focusing system 28, including sensor and control devices (not shown) can be provided which, via optical imaging system 18, automatically maintains wafer 10, and therefore, wafer die(s) 12, in focus. An automatic focusing system, such as system 28, automatically adjusts and sets the position of objective lens 46 of optical imaging system 18 for optimum focus of all wafer dies 12 on wafer 10. Optical imaging system 18 is in communication with the central control system 20 via control/data links 49. During operation of wafer inspection system 9, focusing lens 42 images laser light 48, where laser light 48 represents light reflected, scattered and diffracted by wafer 10, onto focal plane assembly 30. However, the particular arrangement of the auto-focusing system can vary and is not essential to the present subject matter.

Focal plane assembly 30 can include one or more detector ensembles. Each detector ensemble can feature a single or multiple two-dimensional matrix photo-detectors. For example, in some embodiments assembly 30 comprises at least one two-dimensional CCD matrix photo-detector, focal plane assembly electronics 54, and control/data links 56, 58, and 90, enabling high capacity and ultra fast high resolution synchronous imaging of a wafer die 12. Focal plane assembly 30 is in communication with central control system 20 via control/data links 56 and 58.

Figure 10B:
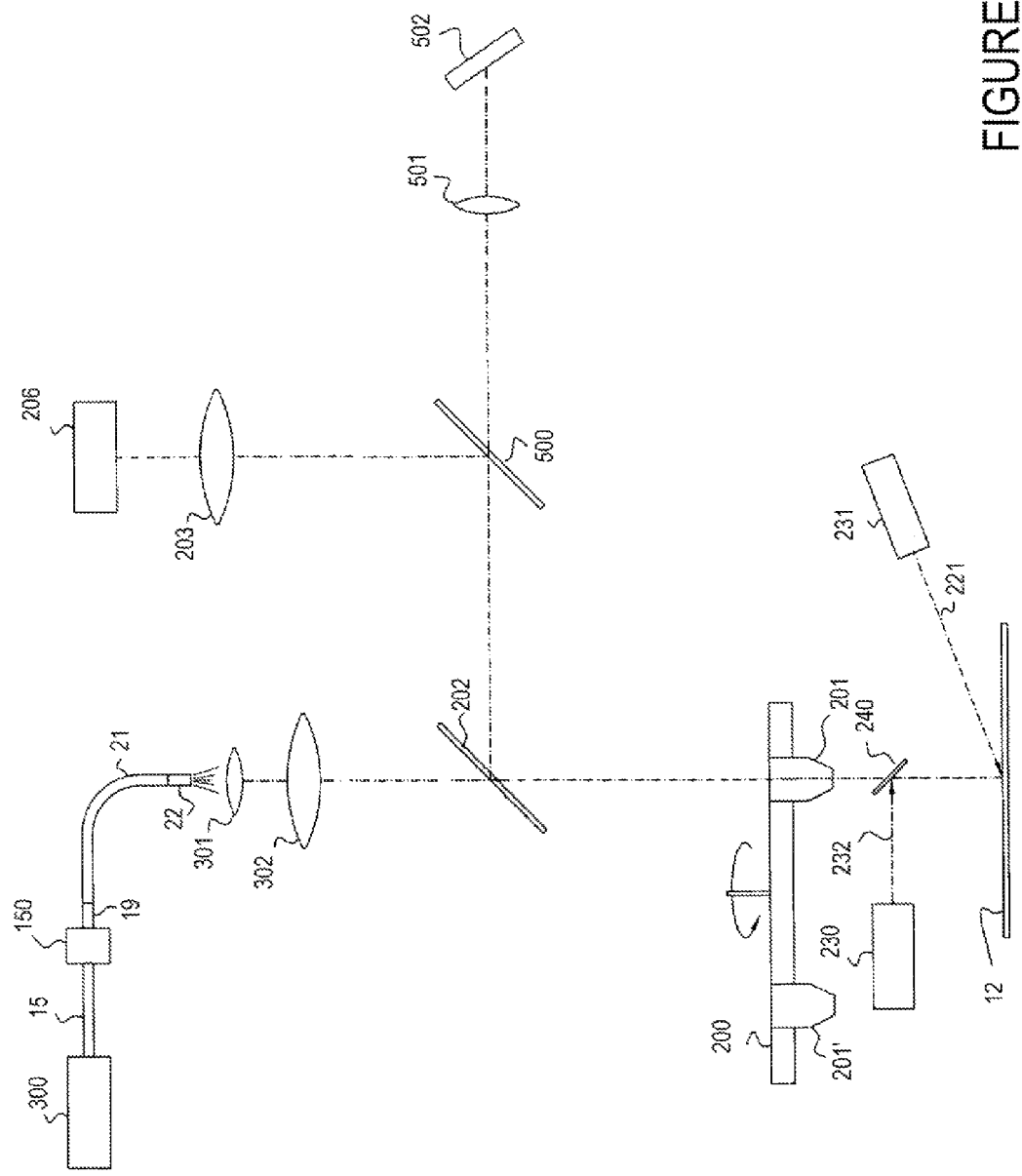
FIG. 10B is a block diagram illustrating illumination and detection components in an exemplary optical inspection system.
Figure 12A:
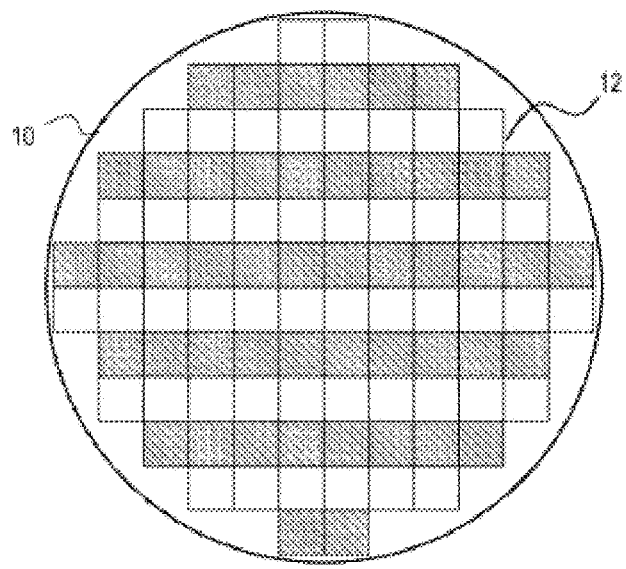
FIG. 12 illustrates three examples of diluted scans.
Figure 12B:
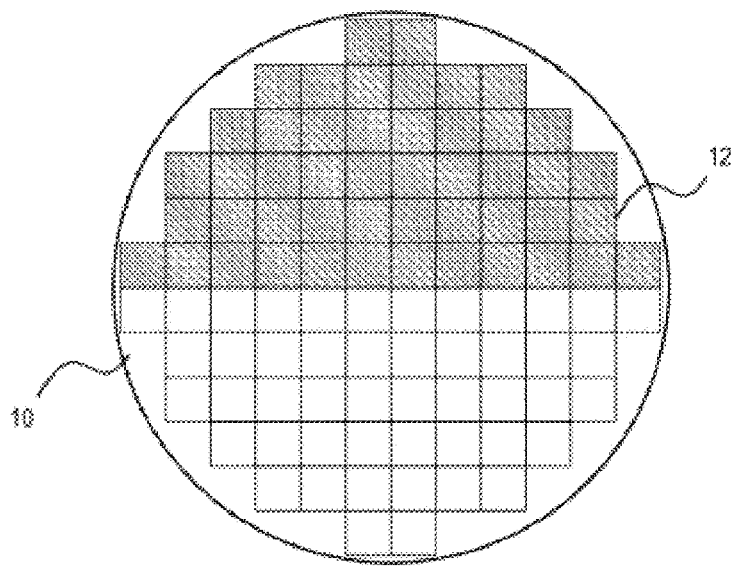
Figure 12C:
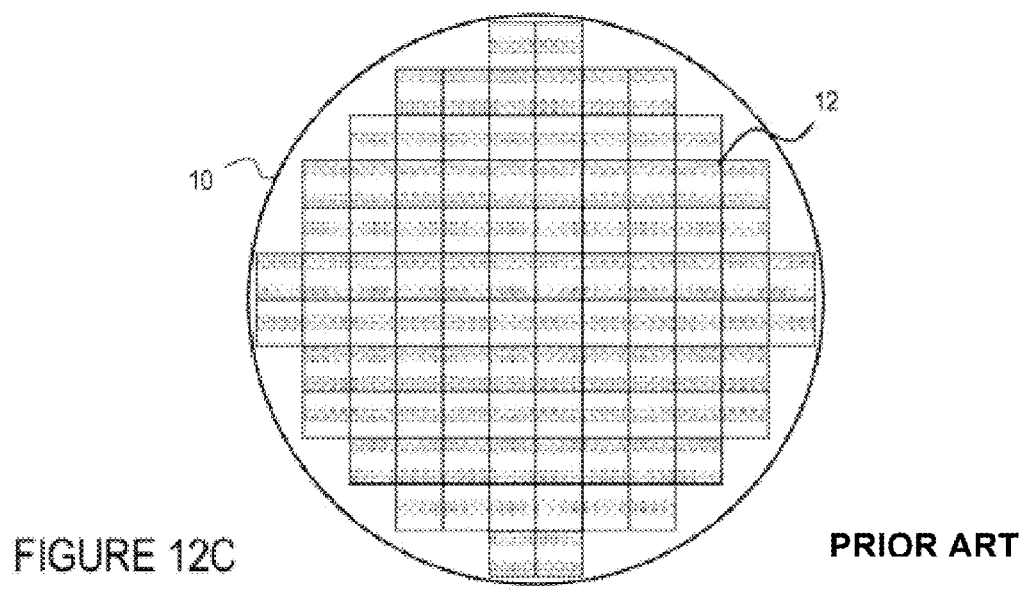

Reference is now made to FIG. 10B, which is an overall schematic side view of components in an illumination system of the defect detection apparatus, according to an exemplary embodiment of the present subject matter. According to different methods of operation, three alternative modes of illumination can be provided: Bright Field (BF), Side-illuminated Dark Field (DF) and Orthogonal or Obscured Reflectance Dark Field (ODF). Each mode of illumination is used to detect different types of defects in different production process steps. For example in order to detect an embedded defect in a transparent layer, such as silicon oxide, BF illumination is preferred. In order to detect a small particle on a surface, DF illumination generally yields better results.

In bright field illumination in general, the illumination is incident on the sample through the same objective lens as is used for viewing the sample. FIG. 10B shows a bright field illuminating laser source 300 delivering its output beam 15 into an optical delivery fiber bundle 21, preferably by means of a laser to fiber coupler 150. This optical fiber bundle 21 provides both uniform illumination on the sample and coherence breaking of the laser illumination. In some embodiments, only a single fiber bundle is used, but it is to be understood that a serial fiber bundle solution may also be suitable. In other embodiments, one or more bundles may be combined with further components, such as a light guide or guides. Discussion of exemplary fiber/light guide combinations can be found in co-pending U.S. Publication 20080027933 entitled "Speckle Reduction Using a Fiber Bundle and Light Guide,"filed Aug. 14, 2006, and incorporated by reference herein for all purposes.

From the output termination of the fiber bundle 21, the laser beam is imaged by means of illumination transfer lenses 301, 302 onto the objective lens in use 201, which is operative to focus the illumination onto a wafer 10 being inspected. Appropriate alternative objective lenses 201' can be swung into place on an objective revolver 200, as is known in the microscope arts. The illumination returned from the wafer is collected by the same objective lens 201, and is deflected from the illumination path by means of a beam splitter 202, towards a second beam splitter 500, from where it is reflected through the imaging lens 203, which images the light from the wafer onto the detector 206. The second beam splitter 500 is used to separate the light going to the imaging functionality from the light used in the auto-focus functionality, which is directed by means of the auto-focus imaging lens 501 to the auto-focus detector 502.

When conventional dark field illumination is required for the imaging in hand, a dark field side illumination source 231 is used to project the required illumination beam 221 onto the wafer 10. When orthogonal dark field, or obscured reflectance dark field illumination is required for the imaging in hand, an alternative dark field illumination source 230 is used to project the required illumination beam 232 via the obscured reflectance mirror 240 onto the wafer 10 orthogonally from above. FIG. 10B indicates sources 300, 231, and 230 at different locations. However, any or all of sources 300, 230, and 231 may comprise the same light source, with the bright field, dark field, and obscured reflectance dark field effects achieved through moving the source(s) and/or redirecting illumination to the appropriate angle using one or more optical components.

In operation, one or more images of the wafer are obtained and the images are evaluated determine the presence or absence of a defect or potential defect in the wafer. For instance, the tool may obtain images on a frame-by-frame basis and compare groups of frames to references. Any suitable comparison technique may be used, including cell-to-cell comparison, die-to-die comparison, and the comparisons may be carried out using any suitable algorithm(s) to analyze the images. Additionally or alternatively, frames or groups of frames may be analyzed independently of comparison to a reference for information indicative of a defect, such as, for example, bright spots in an otherwise-dark area, dark spots in an otherwise-light area, and so on.

Although an exemplary inspection tool was briefly described above, it is intended that the present subject matter be applicable to any type of inspection tool. For example, other inspection tools may utilize different light sources, different imaging components (e.g. different types, numbers, and/or arrangement of detectors and optical components), and/or different components for providing relative motion between the imaging components and the wafer. Furthermore, any suitable type and/or number of inspection methodologies may be used to determine the presence or absence of defects.

It is appreciated by persons skilled in the art that what has been particularly shown and described above is not meant to be limiting, but instead serves to show and teach various exemplary implementations of the present subject matter. As set forth in the attached claims, the scope of the present invention includes both combinations and sub-combinations of various features discussed herein, along with such variations and modifications as would occur to a person of skill in the art.

What is claimed:

1. A method of optical inspection, the method comprising:
positioning at least one wafer for inspection by an optical inspection tool; and
performing, according to a dilution plan, a diluted scan of at least one slice of the wafer, said slice lying along a scanning axis and having a total area, so that at least ten percent of the total area of said slice is not imaged;
wherein: (a) performing the diluted scan comprises scanning, following an inspection path, a plurality of areas in at least one slice, and imaging some, but not all, of the areas in the slice; (b) the dilution plan is formulated based on a dilution parameter indicating an amount of dilution for the at least one slice; and (c) the inspection path is calculated according to at least one of: (i) a desired size for an inspected region of the wafer, (ii) a number of imaging unit areas per inspected region, (iii) a number of slices per inspected region, and (iv) a position of each imaging area relative to an inspected region.

2. The method as set forth in claim 1, further comprising performing a scan of at least one other slice; wherein the at least one other slice is not adjacent to the at least one slice in a perpendicular direction.

3. The method as set forth in claim 1, wherein the method comprises performing a diluted scan of at least a first and second parallel slice of the wafer; and wherein at least one area imaged in the first slice is at a different location along the scanning axis than at least one area imaged in the second slice.

4. The method as set forth in claim 1, wherein the method comprises performing a diluted scan of at least one slice of the wafer so that essentially twenty-five percent of an area of the wafer designated for inspection is imaged.

5. The method as set forth in claim 1, wherein the method comprises performing a diluted scan of at least one slice of the wafer so that essentially fifty percent of an area of the wafer designated for inspection is imaged.

6. The method as set forth in claim 1, wherein the method comprises performing a diluted scan of at least one slice of the wafer so that essentially seventy-five percent of an area of the wafer designated for inspection is imaged.

7. The method as set forth in claim 1, wherein each area comprises a frame.

8. A method of optical inspection, the method comprising:
accessing data comprising an inspection recipe, the inspection recipe designating at least a portion of a wafer of a defined type for inspection using an inspection path calculated according to at least one of: (i) a desired size for the inspected portion of the wafer, (ii) a number of imaging unit areas for the inspected portion of the wafer, (iii) a number of slices per inspected portion of the wafer, and (iv) a position of each imaging area relative to the inspected portion of the wafer; and
performing a diluted scan of the designated portion of each of a plurality of wafers of the defined type; wherein performing each diluted scan comprises scanning, following a respective inspection path for each wafer, a plurality of areas in at least one slice of each wafer, and imaging some, but not all, of the areas in the slice;
wherein the diluted scans are performed in a manner so that at least one area in at least one wafer is imaged and the corresponding area in at least one other wafer is not imaged; and
wherein the diluted scans are performed in a manner so that (i) the imaged areas from the diluted scans, if taken in combination, represent the portion designated for inspection, and (ii) none of a plurality of areas imaged in at least one first wafer are imaged in at least one second wafer and none of a plurality of areas imaged in the at least one second wafer are imaged in the at least one first wafer.

9. The method as set forth in claim 8, wherein the designated portion comprises the entire wafer.

10. A method of inspecting a wafer, the method comprising:
accessing data comprising an inspection recipe, the inspection recipe designating at least a portion of a wafer for inspection using an inspection path calculated according to at least one of: (i) a desired size for the inspected portion of the wafer, (ii) a number of imaging unit areas for the inspected portion of the wafer, (iii) a number of slices per inspected portion of the wafer, and (iv) a position of each imaging area relative to the inspected portion of the wafer; wherein the designated portion comprises a plurality of regions;
performing, according to a dilution plan, a diluted scan of the designated portion of the wafer; wherein performing each diluted scan comprises scanning, following the inspection path, a plurality of areas in at least one slice of the wafer, and imaging some, but not all, of the areas; and wherein the dilution plan is formulated based on a dilution parameter indicating an amount of dilution for the at least one slice;
based on the imaged areas, evaluating the portion designated for inspection for the presence of defects;
for each defect that lies within a region, determining where the defect lies within its respective region relative to a reference point;
projecting each defect from the plurality of regions into a representative region based on each defect's determined location relative to its respective region reference point; and
calculating at least one defect density for at least one part of the region by determining a total number of projected defects in the at least one part of the region and the number of times the part of the region containing the defect was scanned.

11. The method as set forth in claim 10, wherein the region comprises a wafer die.

12. The method as set forth in claim 11, wherein the method comprises calculating a defect density for a plurality of parts of the die; and wherein each part comprises a square millimeter of the die.

13. A method of inspecting a plurality of wafers, the method comprising:
accessing data comprising an inspection recipe, the inspection recipe designating at least a portion of a wafer of a defined type for inspection using an inspection path calculated according to at least one of: (i) a desired size for the inspected portion of the wafer, (ii) a number of imaging unit areas for the inspected portion of the wafer, (iii) a number of slices per inspected portion of the wafer, and (iv) a position of each imaging area relative to the inspected portion of the wafer;
performing, according to a dilution plan, a diluted scan of the designated portion of each of a plurality of wafers of the defined type; wherein performing each diluted scan comprises scanning, following a respective inspection path for each of the plurality of wafers, a plurality of areas in at least one slice of each respective wafer, and imaging some, but not all, of the areas; and wherein the dilution plan is formulated based on a dilution parameter indicating an amount of dilution for the at least one slice;
based on the imaged areas, evaluating the portion designated for inspection in each wafer for the presence of defects;
for each defect, determining where the defect lies relative to a reference point of the wafer;
projecting each defect into a single projected wafer based on each defect's determined location relative to the reference point; and
correcting data regarding the projected defects based at least in part on the number of times the portion of the wafer comprising the defect is scanned.

14. An optical inspection system comprising an imager and at least one illumination source, wherein the optical inspection system comprises processing means for performing, according to a dilution plan, a diluted scan of at least one slice of a wafer, said slice lying along a scanning axis and having a total area, so that at least ten percent of the total area of said slice is not imaged; wherein performing the diluted scan comprises scanning, following an inspection path, a plurality of areas in at least one slice, and imaging some, but not all, of the areas in the slice; wherein the dilution plan is formulated based on a dilution parameter indicating an amount of dilution for the at least one slice; and wherein the inspection path is calculated according to at least one of: (i) a desired size for an inspected portion of the wafer, (ii) a number of imaging unit areas for the inspected portion of the wafer, (iii) a number of slices per inspected portion of the wafer, and (iv) a position of each imaging area relative to the inspected portion of the wafer.

15. The system as set forth in claim 14, wherein the system is further configured to perform a scan of at least one other slice; wherein the at least one other slice is not adjacent to the at least one slice in a perpendicular direction.

16. The system as set forth in claim 14, wherein the system is configured to perform a diluted scan of at least a first and second parallel slice of the wafer so that at least one area imaged in the first slice is at a different location along the scanning axis than at least one area imaged in the second slice.

17. The system as set forth in claim 14, wherein the system is configured to perform a diluted scan of at least one slice of the wafer so that essentially twenty-five percent of an area of the wafer designated for inspection is imaged.

18. The system as set forth in claim 14, wherein the system is configured to perform a diluted scan of at least one slice of the wafer so that essentially fifty percent of an area of the wafer designated for inspection is imaged.

19. An optical inspection tool comprising:
means for accessing data comprising an inspection recipe, the inspection recipe designating at least a portion of a wafer of a defined type for inspection using an inspection path calculated according to at least one of: (i) a desired size for the inspected portion of the wafer, (ii) a number of imaging unit areas for the inspected portion of the wafer, (iii) a number of slices per inspected portion of the wafer, and (iv) a position of each imaging area relative to the inspected portion of the wafer; and
means for performing a diluted scan of the designated portion of each of a plurality of wafers of the defined type;
wherein performing the diluted scan comprises scanning, following the inspection path, a plurality of areas in at least one slice of each wafer, and imaging some, but not all, of the areas in the slice;
wherein the diluted scans are performed in a manner so that at least one area in at least one wafer is imaged and the corresponding area in at least one other wafer is not imaged; and
wherein the diluted scans are performed in a manner so that (i) the imaged areas from the diluted scans, if taken in combination, represent the portion designated for inspection, and (ii) none of a plurality of areas imaged in at least one first wafer are imaged in at least one second wafer and none of a plurality of areas imaged in the at least one second wafer are imaged in the at least one first wafer.

20. The tool as set forth in claim 19, wherein the designated portion comprises the entire wafer.

21. An optical inspection tool comprising:
means for accessing data comprising an inspection recipe, the inspection recipe designating at least a designated portion of a wafer for inspection, said designated portion comprising a plurality of regions, using an inspection path calculated according to at least one of: (i) a desired size for the inspected portion of the wafer, (ii) a number of imaging unit areas for the inspected portion of the wafer, (iii) a number of slices per inspected portion of the wafer, and (iv) a position of each imaging area relative to the inspected portion of the wafer;
means for performing, according to a dilution plan, a diluted scan of the designated portion of the wafer; wherein performing the diluted scan comprises scanning, following the inspection path, a plurality of areas in at least one slice of the wafer, and imaging some, but not all, of the areas and wherein the dilution plan is formulated based on a dilution parameter indicating an amount of dilution for the at least one slice;
means for evaluating the designated portion for the presence of defects based on the imaged areas;
means for determining, for each defect that lies within a region, where the defect lies within its respective region relative to a reference point;
means for projecting each defect from the plurality of regions into a representative region based on each defect's determined location relative to its respective region reference point; and
means for calculating at least one defect density for at least one part of the region by determining a total number of projected defects in the at least one part of the region and the number of times the part of the region containing the defect was scanned.

* * * * *